(12) United States Patent
Komenoi et al.

(10) Patent No.: US 8,198,464 B2
(45) Date of Patent: Jun. 12, 2012

(54) METHOD FOR PRODUCING C-GLYCOSIDE DERIVATIVE AND INTERMEDIATE FOR SYNTHESIS THEREOF

(75) Inventors: Kousuke Komenoi, Chuo-ku (JP); Atsushi Nakamura, Chuo-ku (JP); Makoto Kasai, Chuo-ku (JP); Masakazu Imamura, Chuo-ku (JP); Ryota Shiraki, Chuo-ku (JP); Keita Nakanishi, Chuo-ku (JP)

(73) Assignees: Astellas Pharma Inc., Tokyo (JP); Kotobuki Pharmaceutical Co., Ltd., Nagano (JP)

( * ) Notice: Subject to any disclaimer, the term of this patent is extended or adjusted under 35 U.S.C. 154(b) by 384 days.

(21) Appl. No.: 12/520,484

(22) PCT Filed: Dec. 20, 2007

(86) PCT No.: PCT/JP2007/074516
§ 371 (c)(1),
(2), (4) Date: Jun. 19, 2009

(87) PCT Pub. No.: WO2008/075736
PCT Pub. Date: Jun. 26, 2008

(65) Prior Publication Data
US 2010/0094025 A1 Apr. 15, 2010

(30) Foreign Application Priority Data
Dec. 21, 2006 (JP) .................... 2006-344360

(51) Int. Cl.
*C07D 409/08* (2006.01)
(52) U.S. Cl. .......................................... 549/58
(58) Field of Classification Search .............. 549/58
See application file for complete search history.

(56) References Cited

U.S. PATENT DOCUMENTS

| | | |
|---|---|---|
| 6,414,126 B1 | 7/2002 | Ellsworth et al. |
| 6,515,117 B2 | 2/2003 | Ellsworth et al. |
| 6,617,313 B1 | 9/2003 | Maurya et al. |
| 6,774,112 B2 | 8/2004 | Gougoutas |
| 6,777,392 B2 | 8/2004 | Maurya et al. |
| 7,169,761 B2 | 1/2007 | Tomiyama et al. |
| 7,169,791 B2 | 1/2007 | Breitenstein et al. |
| 7,202,350 B2 | 4/2007 | Imamura et al. |
| 7,338,941 B2 | 3/2008 | Bibbs et al. |
| 7,375,213 B2 | 5/2008 | Deshpande et al. |
| 2001/0041674 A1 | 11/2001 | Tomiyama et al. |
| 2002/0137903 A1 | 9/2002 | Ellsworth et al. |
| 2003/0114390 A1 | 6/2003 | Washburn et al. |
| 2004/0138439 A1 | 7/2004 | Deshpande et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0124555 A1 | 6/2005 | Tomiyama et al. |
| 2005/0209166 A1 | 9/2005 | Eckhardt et al. |
| 2005/0233988 A1 | 10/2005 | Nomura et al. |
| 2006/0009400 A1 | 1/2006 | Eckhardt et al. |
| 2006/0019948 A1 | 1/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0234953 A1 | 10/2006 | Himmelsbach et al. |
| 2006/0234954 A1 | 10/2006 | Urbanski |
| 2006/0251728 A1 | 11/2006 | Himmelsbach et al. |
| 2006/0258749 A1 | 11/2006 | Eckhardt et al. |
| 2006/0293251 A1 | 12/2006 | Urbanski et al. |
| 2007/0004648 A1 | 1/2007 | Himmelsbach et al. |
| 2007/0021510 A1 | 1/2007 | Hickey et al. |
| 2007/0027092 A1 | 2/2007 | Himmelsbach et al. |
| 2007/0049537 A1 | 3/2007 | Eckhardt et al. |
| 2007/0073046 A1 | 3/2007 | Eckhardt et al. |
| 2007/0161787 A1 | 7/2007 | Imamura et al. |
| 2007/0238866 A1 | 10/2007 | Deshpande et al. |
| 2007/0259821 A1 | 11/2007 | Eckhardt et al. |
| 2007/0293690 A1 | 12/2007 | Tomiyama et al. |
| 2008/0004336 A1 | 1/2008 | Gougoutas et al. |
| 2008/0027014 A1 | 1/2008 | Nomura et al. |
| 2008/0058379 A1 | 3/2008 | Eckhardt et al. |
| 2008/0132563 A1 | 6/2008 | Kakinuma et al. |
| 2008/0234366 A1 | 9/2008 | Bindra et al. |
| 2008/0234367 A1 | 9/2008 | Washburn et al. |
| 2008/0319047 A1 | 12/2008 | Matsuoka et al. |
| 2009/0018202 A1 | 1/2009 | Hickey et al. |
| 2009/0069252 A1 | 3/2009 | Imamura et al. |

FOREIGN PATENT DOCUMENTS

DE 2027796 A1 12/1971

(Continued)

OTHER PUBLICATIONS

Canadian Office Action dated May 27, 2011, as issued in Canadian Patent Application No. 2,673,498.
O.N. Tolkachev, et al., "Synthetic Investigations in the Field of Curare Alkaloids", Zhurnal Obshchei Khimii, 1961, pp. 1540-1545, vol. 51, No. 5.
Pauline Rogowska, et al., "Evidence for stong heterodimeric interactions of phenylboronic acids with amino acids", Tetrahedron Letters, 2006, pp. 1389-1393, vol. 47.
International Search Report for PCT/JP2007/074516, dated Feb. 12, 2008.
PCT/ISA/237 for PCT/JP2007/074516, dated Feb. 12, 2008.
Korean Office Action dated Mar. 30, 2011, as issued in Korean Patent Application No. 10-2009-7014320.

(Continued)

*Primary Examiner* — Taofiq A Solola
(74) *Attorney, Agent, or Firm* — Sughrue Mion, PLLC

(57) ABSTRACT

The present invention provides a method for producing a C-glycoside derivative, which can produce the C-glycoside derivative at a high yield and at a low cost, which conforms to environmental protection, and which is applicable industrially. The C-glycoside derivative is useful for treating and preventing diabetes such as insulin-dependent diabetes (type 1 diabetes), non-insulin-dependent diabetes (type 2 diabetes) and the like and various diabetes-related diseases including insulin-resistant diseases and obesity.

7 Claims, No Drawings

FOREIGN PATENT DOCUMENTS

| | | |
|---|---|---|
| JP | 6-199695 A | 7/1994 |
| JP | 2001-288178 A | 10/2001 |
| JP | 2003-511458 A | 3/2003 |
| JP | 2004-359630 A | 12/2004 |
| WO | 98/31697 A1 | 7/1998 |
| WO | 01/27128 A1 | 4/2001 |
| WO | 02/083066 A2 | 10/2002 |
| WO | 03/082887 A1 | 10/2003 |
| WO | 03/087093 A1 | 10/2003 |
| WO | 03/094928 A1 | 11/2003 |
| WO | 03/099836 A1 | 12/2003 |
| WO | 2004/013118 A1 | 2/2004 |
| WO | 2004/063209 A2 | 7/2004 |
| WO | 2004/080990 A1 | 9/2004 |
| WO | 2005/012326 A1 | 2/2005 |
| WO | 2005/023198 A2 | 3/2005 |
| WO | 2006/006496 A1 | 1/2006 |
| WO | 2006/011502 A1 | 2/2006 |
| WO | 2006/034489 A2 | 3/2006 |
| WO | 2006/073197 A1 | 7/2006 |
| WO | 2006/108842 A1 | 10/2006 |
| WO | 2006/117359 A1 | 11/2006 |
| WO | 2006/117360 A1 | 11/2006 |
| WO | 2006/120208 A1 | 11/2006 |
| WO | 2007/000445 A1 | 1/2007 |
| WO | 2007/007628 A1 | 1/2007 |
| WO | 2007/031548 A2 | 3/2007 |
| WO | 2007/093610 A1 | 8/2007 |
| WO | 2007/114475 A1 | 10/2007 |
| WO | 2007/128749 A1 | 11/2007 |
| WO | 2007/136116 A2 | 11/2007 |
| WO | 2008/002824 A1 | 1/2008 |
| WO | 2008/013321 A1 | 1/2008 |
| WO | 2008/020011 A1 | 2/2008 |
| WO | 2008/034859 A1 | 3/2008 |
| WO | 2008/075736 A1 | 6/2008 |
| WO | 2008/116179 A1 | 9/2008 |
| WO | 2008/116195 A2 | 9/2008 |

OTHER PUBLICATIONS

Songping Han, et al., "Dapagliflozin, a Selective SGLT2 Inhibitor, Improves Glucose Homeostasis in Normal and Diabetic Rats", Diabetes, 2008, pp. 1723-1729, vol. 57.

Wei Meng, et al., Discovery of Dapagliflozin: A Potent, Selective Renal Sodium-Dependent Glucose Cotransporter 2 (SGLT2) Inhibitor for the Treatment of Type 2 Diabetes, Journal of Medicinal Chemistry, 2008, pp. 1145-1149, vol. 51.

OG Todoulou, et al., "Synthesis and antiviral activity of some new 1H-1,2,4-triazole derivatives", Eur Journal of Medicinal Chemistry, 1994, pp. 611-620, vol. 29.

J. Grant Buchanan, et al. "Synthesis of C-Glycosyltetrazoles Related to 3-Deoxy-D-arabino-heptulosonic Acid 7-Phosphate (DAHP) Potential Inhibitors of Early Steps in the Shikimate Pathway", Journal of the Chemical Society Perkins Transactions 1, 1992, pp. 2593-2601.

Shambhu D. Varma, et al., "Inhibition of Lens Aldose Reductase by Flavonoids-Their Possible Role in the Prevention of Diabetic Cataracts", Biochemical Pharmacology, 1976, pp. 2505-2513, vol. 25.

Adolfo Andrade-Cetto, et al., "Hypoglycemic effect of *Cecropia obtusifolia* on streptozotocin diabetic rats", Journal of Ethnopharmacology, 2001, pp. 145-149, vol. 78.

Zhu-Fang Shen, et al., "Hypoglycemic Effect of the Combined Use of Puerarin and Aspirin in Mice", Acta Pharmaceutica Sinica, 1985, pp. 863-865, vol. 20, No. 11.

Paulina Rogowska, et al., "Evidence for stong heterodimeric interactions of phenylboronic acids with amino acids", Tetrahedron Letters, 2006, pp. 1389-1393, vol. 47.

METHOD FOR PRODUCING C-GLYCOSIDE DERIVATIVE AND INTERMEDIATE FOR SYNTHESIS THEREOF

TECHNICAL FIELD

The present invention relates to a method for producing a C-glycoside derivative which is useful as a $Na^+$-glucose cotransporter inhibitor for treating and preventing, in particular, diabetes such as insulin-dependent diabetes (type 1 diabetes), non-insulin-dependent diabetes (type 2 diabetes) and the like and various diabetes-related diseases including insulin-resistant diseases and obesity; as well as to an intermediate used for synthesis of the C-glycoside derivative.

BACKGROUND ART

The C-glycoside derivative represented by the formula (1) and its salt [hereinafter, they are referred to as "compound (1)" or "compound of formula (1)" in some cases] is known to be useful for treatment and prevention of diabetes such as insulin-dependent diabetes (type 1 diabetes), non-insulin-dependent diabetes (type 2 diabetes) and the like and various diabetes-related diseases including insulin-resistant diseases and obesity (Patent Literature 1).

[Formula 1]

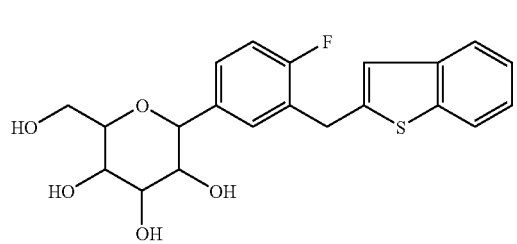

(1)

The method for producing the C-glycoside derivative represented by the formula (1), described in the Patent Literature 1 is understood to be represented by the below-shown reaction formula (I), by referring to the Examples and Reference Examples, described in the Patent Literature 1. Roughly explaining, it is a method which comprises reacting [1-benzothien-2-yl(5-bromo-2-fluorophenyl)methoxy]tert-butyl) dimethylsilane (synthesized in accordance with Reference Example 37 of the Literature) in a manner shown in Example 65 of the Literature, to obtain (1S)-1,5-anhydro-1-[3-(1-benzothien-2-ylmethyl)-4-fluorophenyl]-2,3,4,6-tetra-O-benzyl-D-glucitol and then reacting the obtained compound in accordance with Example 100 of the Literature to synthesize intended (1S)-1,5-anhydro-1-C-[3-(1-benzothiophene-2-ylmethyl)-4-fluorophenyl]-D-glucitol.

Reaction formula (I)

[Formula 2]

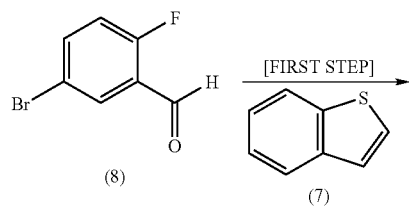

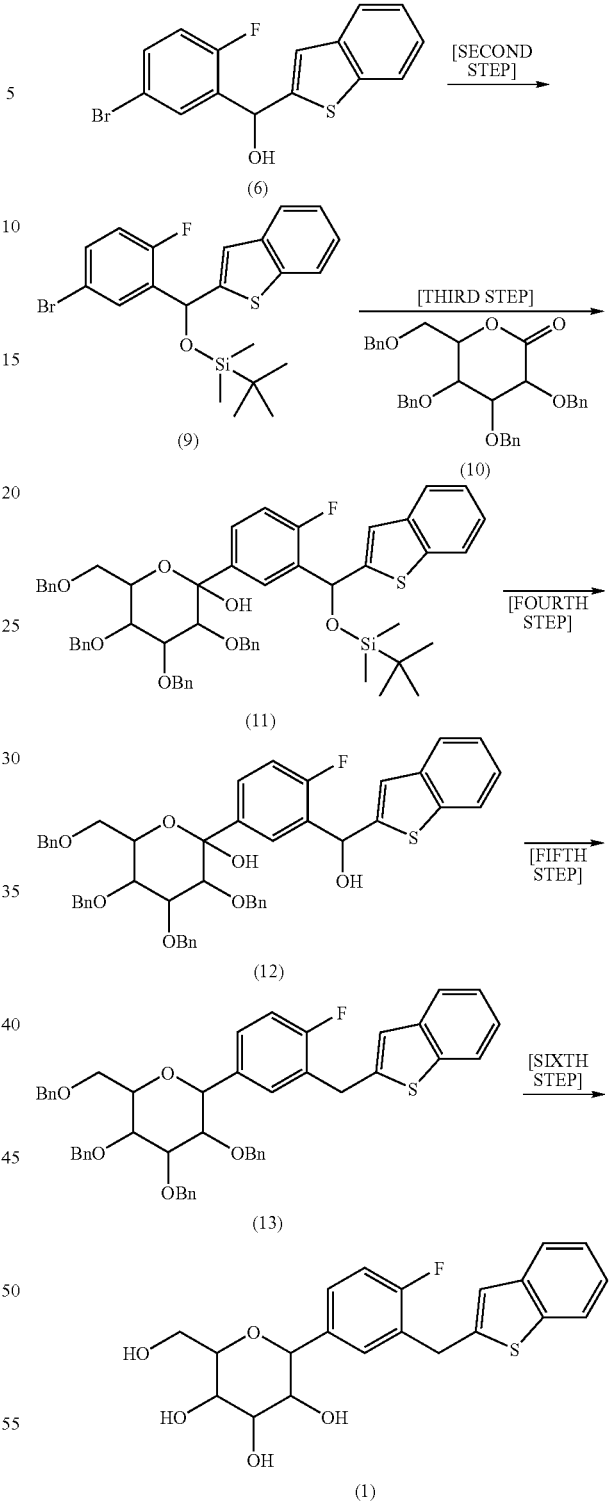

However, the method for producing the C-glycoside derivative of the formula (1), disclosed in the Patent Literature 1 is not industrially satisfactory in yield and cost, as is seen in later-shown Reference Example 1 of the present Description.

For example, as described later, the method includes a step of low product yield (for example, a step of about 50% or lower yield) and the overall yield of the C-glycoside derivative (final product) represented by the formula (1) from the compound (8) (starting raw material) is below 7%; therefore, the method has problems in yield and cost from the standpoint of medicine production and has not been satisfactory industrially. In addition, the method includes an operation of purification by column chromatography which uses chloroform as part of purification solvents; use of such a solvent poses a problem in environmental protection and there are various restrictions in industrial application of such an operation; thus, the method has problems in providing an effective medicine.

Also, an improved method of conducting an addition reaction with trimethylsilyl carbohydrate instead of benzyl carbohydrate and then conducting deprotection for acetylation, is known for a compound which has a structure different from that of the compound of the formula (1) but has a structure common to that of the compound of the formula (1) (Patent Literature 2). It is described in the Patent Literature 2 that the improved method enhances the overall yield to 6.2% from 1.4%. Even in the improved method, however, the yield is low at 6.2% which is far from satisfaction in industrial production.

Patent Literature 1: WO 2004/080990 Pamphlet
Patent Literature 2: WO 2006/006496 Pamphlet

DISCLOSURE OF THE INVENTION

The present invention aims at providing a method for producing a C-glycoside derivative represented by the formula (1), which enables production of the C-glycoside derivative at a high yield and at a low cost, which conforms to environmental protection, and which is advantageous industrially; and an intermediate useful for production of the C-glycoside derivative.

In order to achieve the above aim, the present inventors made a study on the method for industrial production of the compound (1). As a result, the present inventors found, by using a particular intermediate for synthesis, a method for producing a C-glycoside derivative, which requires no purification by column chromatography, which can avoid the use of chlorine-based solvent, which enables production of the C-glycoside derivative at a high yield (an improved overall yield) and at a low cost, which conforms to environmental protection, and which is advantageous industrially. The finding has led to the completion of the present invention. Thus, the present invention provides a method for producing a C-glycoside derivative and an intermediate for synthesis of the C-glycoside derivative, both shown below.

[1] A compound represented by the following formula (2d)

[formula 3]

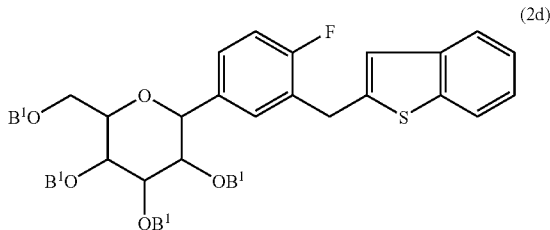

[in the formula, $B^1$s may be the same or different from each other and are each H or $C(=O)R^1$ ($R^1$s may be the same or different from each other and are each lower alkyl), with a proviso that at least one of $B^1$s is $C(=O)R^1$].

[2] A compound according to [1], wherein each $R^1$ is methyl.

[3] A compound represented by the following formula (Ia)

[formula 4]

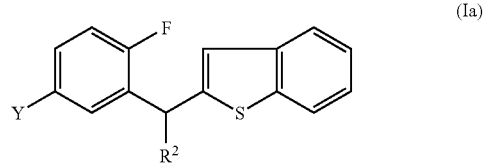

(in the formula, $R^2$ is H or halogen and Y is Br or I).

[4] A method for producing a compound represented by the following formula (1),

[formula 5]

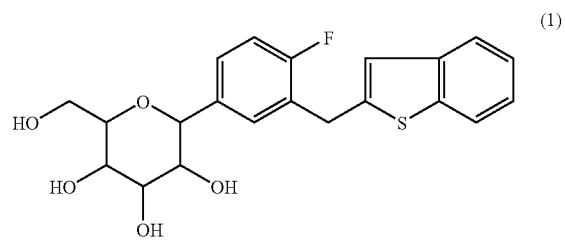

characterized by subjecting the compound set forth in [1] to a reaction for elimination of acyl group.

[5] A method for producing a compound set forth in [1], characterized by allowing a compound selected from the group consisting of triethylsilane, triisopropylsilane, tert-butyldimethylsilane, sodium borohydride and sodium tri(acetoxy)borohydride to act on a compound represented by the following formula (2c)

[formula 6]

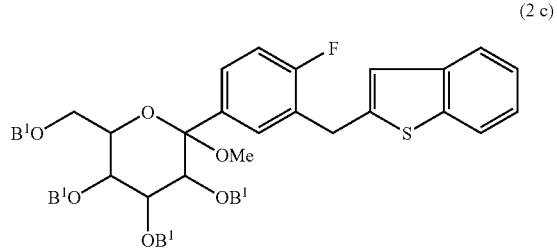

[in the formula, $B^1$s may be the same or different from each other and are each H or $C(=O)R^1$ ($R^1$s may be the same or different from each other and are each lower alkyl) and Me is methyl, with a proviso that at least one of $B^1$s is $C(=O)R^1$], to reduce the compound of the formula (2c).

[6] A method according to [4], wherein the compound set forth in [1] is a compound produced by the method set forth in [5].

[7] A method for producing a compound represented by the following formula (1),

[formula 7]

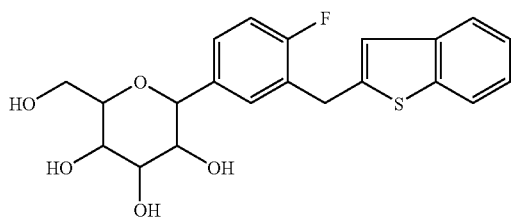

(1)

characterized by subjecting the compound set forth in [2] to a reaction for elimination of acetyl group.

[8] A method for producing a compound set forth in [2], characterized by allowing a compound selected from the group consisting of triethylsilane, triisopropylsilane, tert-butyldimethylsilane, sodium borohydride and sodium tri(acetoxy)borohydride to act on a compound represented by the following formula (2b)

[formula 8]

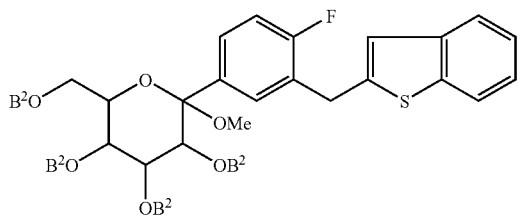

(2b)

[in the formula, $B^2$s may be the same or different from each other and are each H or C(=O)Me and Me is methyl, with a proviso that at least one of $B^2$s is C(=O)Me], to reduce the compound of the formula (2b).

[9] A method according to [7], wherein the compound set forth in [2] is a compound produced by the method set forth in [8].

[10] A method for producing a compound represented by the following formula (1),

[formula 12]

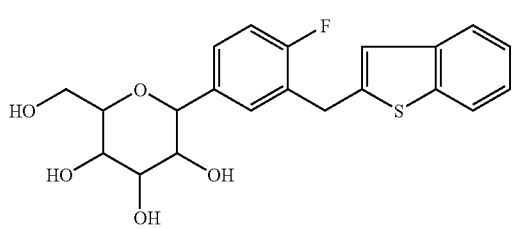

(1)

characterized by subjecting a compound represented by the following formula (4)

[formula 9]

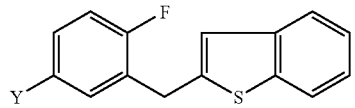

(4)

(in the formula, Y is Br or I) and a compound represented by the following formula (3)

[formula 10]

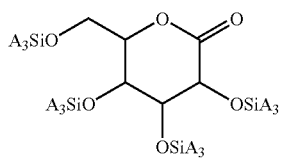

(3)

(in the formula, As may be the same or different from each other and are each lower alkyl), to an addition reaction, eliminating tri-lower alkyl silyl, and being acylated, then conducting reduction to obtain a compound represented by the following formula (2d)

[formula 11]

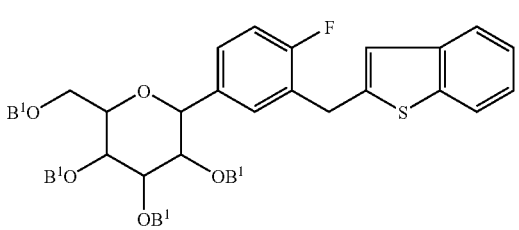

(2d)

[in the formula, $B^1$s may be the same or different from each other and are each H or C(=O)$R^1$ ($R^1$s may be the same or different from each other and are each lower alkyl), with a proviso that at least one of $B^1$s is C(=O)$R^1$], and subjecting the compound to a reaction for elimination of acyl group.

[11] A method according to [10], wherein the compound represented by the formula (4) is a compound of the formula (4) obtained by subjecting a compound represented by the following formula (5)

[formula 13]

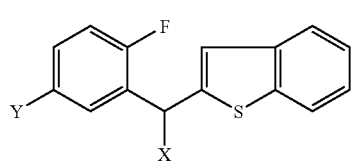

(5)

(in the formula, X is halogen and Y is Br or I) to a reduction reaction.

[12] A method for producing a compound represented by the following formula (1),

[formula 17]

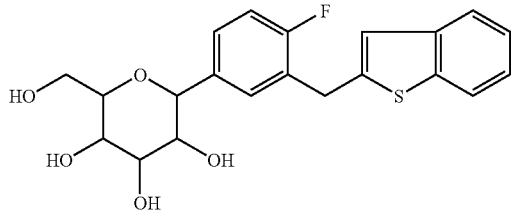

(1)

characterized by subjecting a compound represented by the following formula (4)

[formula 14]

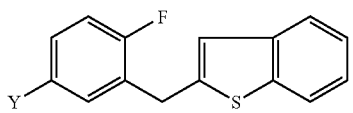

(4)

(in the formula, Y is Br or I) and a compound represented by the following formula (3a)

[formula 15]

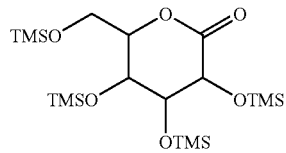

(3a)

(in the formula, TMS is trimethylsilyl) to an addition reaction, eliminating trimethylsilyl in methanol, and being acetylated, then conducting reduction to obtain a compound represented by the following formula (2a)

[formula 16]

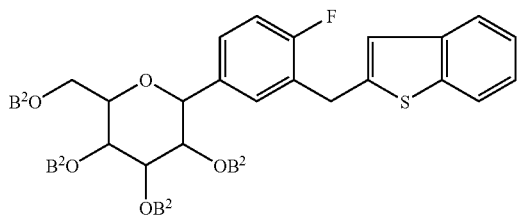

(2a)

[in the formula, $B^2$s may be the same or different from each other and are each H or C(=O)Me (Me is methyl), with a proviso that at least one of $B^2$s is C(=O)Me], and subjecting the compound to a reaction for elimination of acetyl group.

[13] A method according to [12], wherein the compound represented by the formula (4) is a compound of the formula (4) obtained by subjecting a compound represented by the following formula (5)

[formula 18]

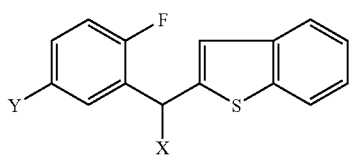

(5)

(in the formula, X is halogen and Y is Br or I) to a reduction reaction.

According to the present invention, there are provided a method for producing a C-glycoside derivative, which enables production of the C-glycoside derivative at a high yield and at a low cost, which conforms to environmental protection, and which is advantageous industrially; and an intermediate for synthesis, which is useful for production of the C-glycoside derivative.

BEST MODE FOR CARRYING OUT THE INVENTION

An embodiment (the first step to the fifth step) of the method for producing a C-glycoside derivative, of the present invention is shown in the following reaction formula (II). Then, each step is described specifically in the order of the first step to the fifth step.

Reaction formula (II)

[Formula 19]

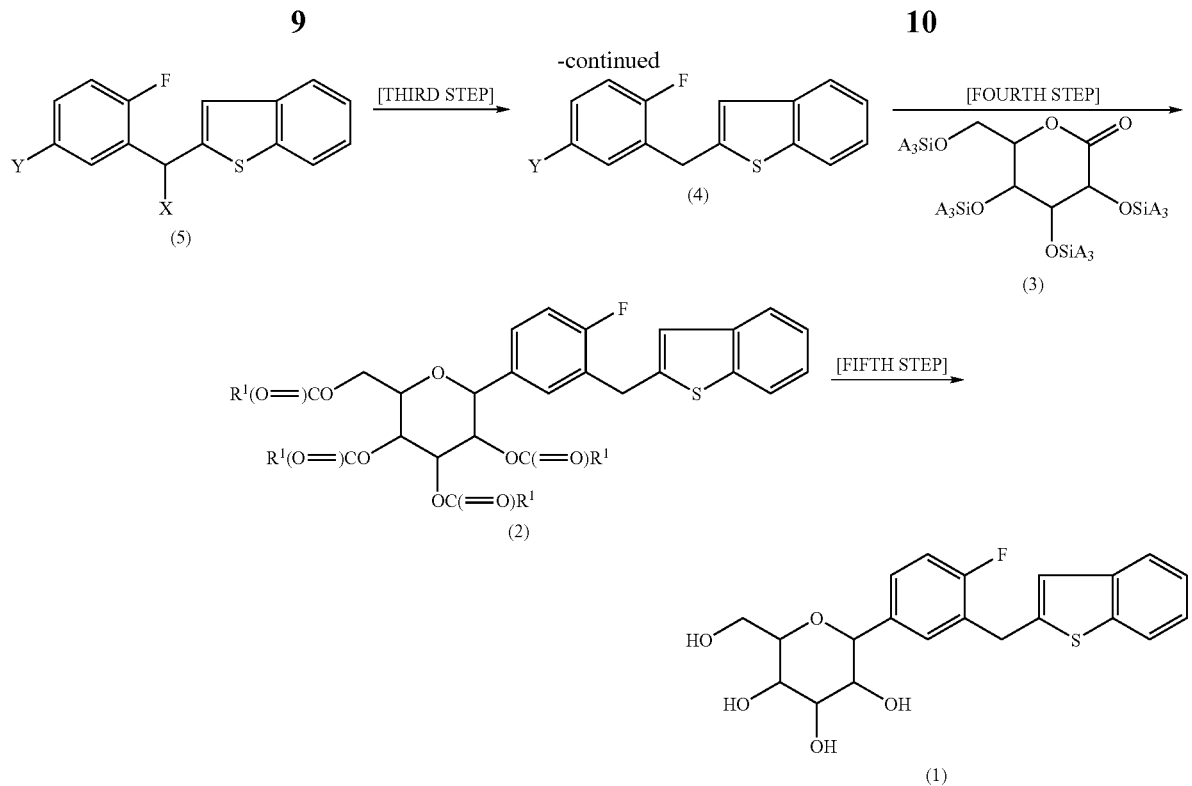

First Step

The first step shown in the reaction formula (II) is a step of conducting an addition reaction with a compound of formula (7) [hereinafter, this compound may be referred to as "compound (7)"] and a compound of formula (8) [hereinafter, this compound may be referred to as "compound (8)". In the reaction formula (II), Y is Br or I and, in an embodiment, is Br. The same applies to hereinafter.] in the presence of an alkyl lithium reagent in an appropriate solvent to obtain a compound of formula (6) [hereinafter, this compound may be referred to as "compound (6)"].

In the addition reaction, as the alkyl lithium reagent, there can be mentioned n-butyl lithium, sec-butyl lithium, tent-butyl lithium, etc.; and, in an embodiment, n-butyl lithium is used. As the solvent, there can be mentioned ethers such as diethyl ether, diisopropyl ether, tetrahydrofuran, 1,4-dioxane, diglyme and the like, and aromatic hydrocarbons such as benzene, toluene, xylene and the like; and, in an embodiment, tetrahydrofuran is used. The reaction can be conducted by adding, to a tetrahydrofuran solution of a compound (7), about 1 equivalent, for example, 0.95 to 1.20 equivalents of n-butyl lithium and conducting a reaction at −80 to −10° C. (−35 to −10° C. in an embodiment) ordinarily for 30 minutes, and adding, to the reaction mixture, about 1 equivalent, for example, 0.95 to 1.20 equivalents of a compound (8) at −80 to −10° C. (−35 to −10° C. in an embodiment). The reaction is complete at −20° C. ordinarily in 1 to 3 hours. To the reaction mixture are added water and hydrochloric acid, followed by extraction; the organic layer is washed with water and subjected to distillation under reduced pressure; to the residue are added toluene and n-heptane; the separated-out crystals are collected by filtration and dried; thereby, a compound (6) can be obtained.

Second Step

The second step shown in the reaction formula (II) is a step of producing a compound of formula (5) [hereinafter, this compound may be referred to as "compound (5)"] from the compound (6) which is a raw material. More particularly, the second step is a step of halogenating the compound (6) (the halogen used in the halogenation is F, Cl, Br or I and, in an embodiment, is Cl) to produce a compound (5). The halogenation is conducted using an appropriate halogenating agent, in an appropriate solvent. As the halogenating agent, there can be mentioned thionyl chloride, thionyl bromide, methanesulfonyl chloride, methanesulfonyl bromide, bromine, iodine, etc., and, in an embodiment, thionyl chloride is used. As the solvent, there can be mentioned aromatic hydrocarbons, ethers, acetonitrile, etc. and, in an embodiment, acetonitrile is used. A pyridine derivative such as pyridine, lutidine or the like, or a tertiary amine such as triethylamine, diisopropylamine or the like may be added. Specifically, the second step can be conducted by dropping, into an acetonitrile solution of the compound (6), an equivalent to excess equivalents, for example, 1 to 1.5 equivalents of thionyl chloride at room temperature to a reflux temperature, at room temperature in an embodiment, followed by stirring ordinarily for 1 to 2 hours.

Third Step

The third step shown in the reaction formula (II) is step of producing a compound of formula (4) [hereinafter, this compound may be referred to as "compound (4)"] from the compound (5) which is a starting material. More particularly, the third step is a step of reducing the compound (5) to produce a compound (4). The reduction is conducted using an appropriate reducing agent, in the presence of a base in an appropriate solvent. As the reducing agent, there can be mentioned sodium borohydride, sodium tri(acetoxy)borohydride etc. and, in an embodiment, sodium borohydride is used. As the base, there can be mentioned metal hydroxides such as sodium hydroxide, potassium hydroxide and the like and, in an embodiment, sodium hydroxide is used. As the solvent, there can be mentioned aromatic hydrocarbons, ethers, acetonitrile, water and mixtures thereof and, in an embodiment, a mixed solvent of acetonitrile and water is used. Specifically, the reaction is conducted by dropping a solution of the compound (5) into an aqueous solution of 0.1 to 2.5 equivalents of sodium hydroxide and an excess amount, for example, 2 to 4 equivalents of sodium borohydride at room temperature to reflux temperature (in an embodiment, at 50 to 70° C.), followed by stirring ordinarily for 1 to 5 hours.

Fourth Step

The fourth step shown in the reaction formula (II) is a step of conducting an addition reaction with the compound (4) and a compound of formula (3) [hereinafter, this compound may be referred to as "compound (3)". In the formula (3), As may be the same or different from each other and are each a linear or branched lower alkyl group of 1 to 6 carbon atoms and, in an embodiment, are each methyl] in the presence of an alkyl lithium reagent in an appropriate solvent, then treating the addition product with an acid in the presence of methanol to remove tri-lower alkylsilyl, then treating the resulting compound with an acylating agent capable of introducing a group represented by formula $R^1C(=O)$ (in the formula, $R^1$ is a linear or branched lower alkyl of 1 to 6 carbon atoms and, in an embodiment, is methyl), to give rise to acylation, then conducting reduction to obtain a compound of formula (2) [hereinafter, this compound may be referred to as "compound (2)"]. Here, the linear or branched lower alkyl of 1 to 6 carbon atoms refers to methyl, ethyl, n-propyl, isopropyl, n-butyl, isobutyl, tert-butyl, n-pentyl, isopentyl, n-hexyl, isohexyl, or the like. In this step, there may be formed, besides the compound (2), such compounds as, in the compound (2), at least one $OC(=O)R^1$ group of the four $OC(=O)R^1$ groups is OH group, and a compound (1) can be obtained also from such compounds by conducting the treatment of fifth step.

In the addition reaction, as the alkyl lithium reagent, there can be mentioned n-butyl lithium, sec-butyl lithium, tert-butyl lithium, etc. and, in an embodiment, n-butyl lithium is used. As the solvent, there can be mentioned ethers and aromatic hydrocarbons and, in an embodiment, a mixed solvent of diisopropyl ether and toluene is used. The reaction can be conducted by adding, to a toluene-diisopropyl ether (1.3:1) solution of the compound (4), about 1 equivalent, for example, 0.95 to 1.20 equivalents of an alkyl lithium reagent, reacting them at −80 to −10° C. (−35 to −20° C. in an embodiment) ordinarily for 0.1 to 5 hours, and adding the reaction mixture to a toluene solution of about 1 equivalent, for example, 0.95 to 1.20 equivalents of a compound (3), in an embodiment, at −80 to −50° C. The reaction is complete at −80 to −50° C. ordinarily in 2 to 24 hours.

In the subsequent step of acid treatment in the presence of methanol, as the acid, there can be mentioned hydrogen chloride, sulfuric acid, acetic acid, trifluoroacetic acid, methanesulfonic acid, p-toluenesulfonic acid, etc. and, in an embodiment, hydrogen chloride is used. The acid treatment by the above acid can be conducted at −5 to 5° C. ordinarily for 1 to 48 hours.

The subsequent acylation step including an acetylation step using an acetylating agent is conducted by conducting a reaction in an appropriate solvent in the presence of an appropriate base, using an acylating agent capable of introducing a group represented by formula $R^1C(=O)$ (in the formula, $R^1$ has the same definition as given above). As the solvent, there can be mentioned ketones such as acetone, 2-butanone and the like; aromatic hydrocarbons; acetic acid esters such as ethyl acetate, isopropyl acetate and the like; aprotic polar solvents such as dimethylformamide, dimethylacetamide and the like; halogenated hydrocarbons such as methylene chloride, chloroform, 1,2-dichloroethane and the like; pyridine; water; and so forth. In an embodiment, toluene is used. As the base, there can be mentioned metal hydroxides such as sodium hydroxide, potassium hydroxide and the like; metal carbonates such as sodium carbonate, potassium carbonate and the like; metal alkoxides such as sodium methoxide, sodium ethoxide, tert-butoxy potassium and the like; metal hydrides such as sodium hydride and the like; tertiary amines such as triethylamine, diisopropylethylamine and the like; pyridine derivatives such as pyridine, lutidine and the like; and so forth. In an embodiment, pyridine is used. As the acylating agent capable of introducing a group represented by formula $R^1C(=O)$ (in the formula, $R^1$ has the same definition as given above), there can be mentioned alkanoic acid anhydrides such as propionic anhydride, propionyl chloride, butyric anhydride and the like; and alkyl halides such as acetyl chloride, acetyl bromide and the like. Of them, preferably used is an acylating agent wherein $R^1$ is methyl of 1 carbon atom, that is, an acetylating agent. As the acetylating agent, there can be mentioned acetyl chloride, acetyl bromide, acetic anhydride, etc. and, in an embodiment, acetic anhydride is used.

The reaction is conducted by adding toluene to the above-mentioned concentration residue and then reacting with an excess amount, for example, 5 equivalents of acetic anhydride in the presence of an excess amount, for example, 6 equivalents of pyridine with cooling or at room temperature. The reaction is complete ordinarily in 1 to 24 hours. A catalytic amount of 4-dimethylaminopyridine may be added for promotion of the reaction.

The subsequent reduction reaction is conducted with an appropriate reducing agent in the presence of an acid catalyst in an appropriate solvent. As the reducing agent, there can be mentioned triethylsilane, triisopropylsilane, tert-butyldimethylsilane, sodium borohydride, sodium tri(acetoxy)borohydride etc. and, in an embodiment, tert-butyldimethylsilane is used. As the acid, there can be mentioned Lewis acids such as boron trifluoride-diethyl ether complex, trimethylsilyl trifluoromethanesulfonate and the like; and Brønsted acids such as acetic acid, trifluoroacetic acid, trifluoromethanesulfonic acid and the like. In an embodiment, trifluoromethanesulfonic acid is used. As the solvent, there can be mentioned halogenated hydrocarbons, ethers, acetonitrile, etc. and, in an embodiment, acetonitrile is used.

Specifically, the reaction is conducted in the presence of an equivalent amount to an excess amount, for example, 1 to 2 equivalents of tert-butyldimethylsilane and an excess amount, for example, 2 equivalents of trifluoromethanesulfonic acid, in an appropriate solvent under cooling or at room temperature, for example, at −5 to 5° C. The reaction is complete ordinarily in 1 to 5 hours.

Fifth Step

The fifth step shown in the reaction formula (II) is a step of obtaining an intended compound of formula (1) from the compound (2) which is a starting material. More particularly, the fifth step is a step of removing acyl group from the compound (2) to produce a compound (1). This reaction is conducted in the presence of an appropriate base in an appropriate solvent. As the base, there can be mentioned metal hydroxides such as sodium hydroxide, potassium hydroxide and the like; metal alkoxides such as sodium methoxide, sodium ethoxide and the like; and so forth. In an embodiment, sodium hydroxide is used. As the solvent, there can be mentioned alcohols such as methanol, ethanol, isopropanol and the like; aromatic hydrocarbons; ethers; water; and mixed solvents thereof. In an embodiment, a methanol-water mixed solvent is used. Specifically, this deprotection reaction is conducted by reacting the compound (2) with, for example, 5 equivalents of sodium hydroxide in an appropriate solvent, for example, a methanol-water mixed solvent at room temperature to a reflux temperature, for example, at 40 to 50° C. The reaction is complete ordinarily in 1 to 5 hours.

Incidentally, the compound (5) and the compound (4) obtained in the second step and the third step, respectively, are both shown by the following formula (1a).

[formula 20]

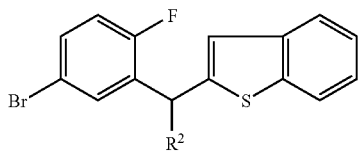

(Ia)

(In the formula, $R^2$ is H or halogen.)

Next, the known method for producing the C-glycoside derivative represented by the formula (1), shown in the reaction formula (I) is explained specifically in the following Reference Example 1.

Reference Example 1

First step: synthesis of 1-benzothien-2-yl(5-bromo-2-fluorophenyl)methanol

Into a tetrahydrofuran (20 ml) solution of benzo[b]thiophene (5.0 g) was dropwise added a n-hexane solution (25 ml) of n-butyl lithium (1.58 M) at −78° C. in an argon atmosphere, followed by stirring at −78° C. for 10 minutes. Into this solution was dropwise added a tetrahydrofuran (80 ml) solution of 5-bromo-2-fluorobenzaldehyde (8.0 g), followed by stirring at −78° C. for 2.5 hours. The temperature of the reaction mixture was elevated to room temperature. Water was added thereto, followed by extraction with ethyl acetate. The organic layer was washed with a saturated aqueous sodium chloride solution, dried over anhydrous magnesium sulfate, filtered, and concentrated. The residue was purified by silica gel column chromatography (n-hexane/ethyl acetate) to obtain 1-benzothien-2-yl(5-bromo-2-fluorophenyl)methanol (10.5 g, yield: 83.6%).

$^1$H-NMR (CDCl$_3$): δ 2.74 (1H, d), 6.35 (1H, d), 6.93 (1H, dd), 7.14 (1H, s), 7.27-7.38 (2H, m), 7.39 (1H, m), 7.68 (1H, dd), 7.74 (2H, m)

Second step: synthesis of [1-benzothien-2-yl(5-bromo-2-fluorophenyl)methoxy](tert-butyl)dimethylsilane To a dimethylformamide (20 ml) solution of 1-benzothien-2-yl(5-bromo-2-fluorophenyl)methanol (5.0 g) were added imidazole (1.3 g), a catalytic amount of 4-(dimethylamino)pyridine and tert-butyldimethylchlorosilane (2.7 g), followed by stirring at room temperature for 7 hours. To the reaction mixture was added a saturated aqueous ammonium chloride solution, followed by extraction with ethyl acetate. The organic layer was washed with a saturated aqueous ammonium chloride solution and a saturated aqueous sodium chloride solution, dried over anhydrous magnesium sulfate, filtered and concentrated. The residue was purified by silica gel column chromatography (n-hexane/ethyl acetate) to obtain [1-benzothien-2-yl(5-bromo-2-fluorophenyl)methoxy](tert-butyl)dimethylsilane (5.22 g, yield: 78.0%).

MS: 451 (M$^+$)

$^1$H-NMR (CDCl$_3$): δ 0.05 (3H, s), 0.11 (3H, s), 0.95 (9H, s), 6.34 (1H, s), 6.91 (1H, t), 7.08 (1H, d), 7.23-7.38 (2H, m), 7.64-7.68 (1H, m), 7.75-7.28 (2H, m)

Third step: Synthesis of 1-C-[3-(1-benzothien-2-yl{[tert-butyl-(dimethyl)silyloxy}methyl)-4-fluorophenyl]-2,3,4,6-tetra-O-benzyl-D-glucopyranose Into a tetrahydrofuran (15 ml) solution of [1-benzothien-2-yl(5-bromo-2-fluorophenyl)methoxy](tert-butyl)dimethylsilane (1.5 g) was dropwise added a n-hexane solution (2.2 ml) of n-butyl lithium (1.58 M) in an argon atmosphere at −78° C., followed by stirring at −78° C. for 30 minutes. Into the solution was dropwise added a tetrahydrofuran (20 ml) solution of 2,3,4,6-tetra-O-benzyl-D-glucono-1,5-lactone (1.9 g), followed by stirring at −78° C. for 15 minutes and then at 0° C. for 1.5 hours. To the reaction mixture was added a saturated aqueous ammonium chloride solution, followed by extraction with ethyl acetate. The organic layer was washed with a saturated aqueous ammonium chloride solution and a saturated aqueous sodium chloride solution, dried over anhydrous magnesium sulfate, filtered and concentrated. The residue was purified by silica gel column chromatography (n-hexane/chloroform/acetone) to obtain 1-C-[3-(1-benzothien-2-yl{[tert-butyl-(dimethyl)silyloxy}methyl)-4-fluorophenyl]-2,3,4,6-tetra-O-benzyl-D-glucopyranose (1.52 g, yield: 50.2%).

MS: 933 (M+Na)

Fourth step: Synthesis of 1-C-{3-[1-benzothien-2-yl(hydroxy)methyl]-4-fluorophenyl}-2,3,4,6-tetra-O-benzyl-D-glucopyranose To a tetrahydrofuran (15 ml) solution of 1-C-[3-(1-benzothien-2-yl{[tert-butyl-(dimethyl)silyloxy}methyl)-4-fluorophenyl]-2,3,4,6-tetra-O-benzyl-D-glucopyranose (1.52 g) was added a tetrahydrofuran solution (2.0 ml) of tetrabutylammonium fluoride (1.0 M), followed by stirring at room temperature for 1 hour. The reaction mixture was concentrated per se. The residue was purified by silica gel column chromatography (n-hexane/ethyl acetate) to obtain 1-C-{3-[1-benzothien-2-yl(hydroxy)methyl]-4-fluorophenyl}-2,3,4,6-tetra-O-benzyl-D-glucopyranose (0.99 g, yield: 74.7%).

MS: 819 (M+Na), 779 (M+H−H$_2$O)

Fifth step: Synthesis of (1S)-1,5-anhydro-1-[3-(1-benzothien-2-ylmethyl)-4-fluorophenyl]-2,3,4,6-tetra-O-benzyl-D-glucitol To an acetonitrile (5.0 ml) solution of 1-C-{3-[1-benzothien-2-yl(hydroxy)methyl]-4-fluorophenyl}-2,3,4,6-tetra-O-benzyl-D-glucopyranose (500 mg) were added triethylsilane (175 mg) and boron trifluoride-diethyl ether complex (196 mg) in an argon atmosphere at −20° C., followed by stirring at −20° C. for 5 hours. To the reaction mixture was added a saturated aqueous sodium bicarbonate solution, followed by extraction with chloroform. The organic layer was washed with a saturated aqueous sodium bicarbonate solution and a saturated aqueous sodium chloride solution, dried over anhydrous magnesium sulfate, filtered and concentrated. The residue was purified by silica gel column chromatography (n-hexane/ethyl acetate) to obtain (1S)-1,5-anhydro-1-[3-(1-benzothien-2-ylmethyl)-4-fluorophenyl]-2,3,4,6-tetra-O-benzyl-D-glucitol (150 mg, yield: 30.2%)

MS: 787 (M+Na)

¹H-NMR (CDCl₃): δ 3.42-3.48 (1H, m), 3.55-3.58 (1H, m), 3.72-3.78 (4H, m), 3.83 (1H, d), 4.14-4.30 (3H, m), 4.39 (1H, d), 4.51-4.67 (4H, m), 4.83-4.94 (2H, m), 6.86-6.90 (1H, m), 6.98 (1H, brs), 7.06-7.37 (24H, m), 7.57-7.60 (1H, m), 7.66-7.69 (1H, m)

Sixth step: Synthesis of (1S)-1,5-anhydro-1-C-[3-(1-benzothiophene-2-ylmethyl)-4-fluorophenyl]-D-glucitol To a dichloromethane (10 ml) solution of (1S)-1,5-anhydro-1-[3-(1-benzothien-2-ylmethyl)-4-fluorophenyl]-2,3,4,6-tetra-O-benzyl-D-glucitol (137 mg) were added pentamethylbenzene (382 mg) and a n-heptane solution (0.75 ml) of boron trichloride (1.0 M) in an argon atmosphere at −78° C., followed by stirring at −78° C. for 3 hours. Methanol was added to the reaction mixture, the temperature of the resulting mixture was elevated to room temperature, and the mixture was concentrated per se. The residue was purified by silica gel column chromatography (chloroform/methanol) to obtain (1S)-1,5-anhydro-1-C-[3-(1-benzothiophene-2-ylmethyl)-4-fluorohenyl]-D-glucitol (63 mg, yield: 87.8%).

¹H-NMR (CD₃OD): δ 3.29-3.48 (4H, m), 3.68 (1H, dd), 3.87 (1H, dd), 4.11 (1H, d), 4.20-4.29 (2H, m), 7.03 (1H, s), 7.08 (1H, dd), 7.19-7.29 (2H, m), 7.35 (1H, m), 7.42 (1H, dd), 7.64 (1H, d), 7.72 (1H, d)

Reference Example 2

Synthesis of
2-(5-bromo-2-fluorobenzyl)-1-benzothiophene
[synthesis of compound (4)]

In the third step of the production method of the present invention, when a compound (4) is separated out as crystals, a seed crystal of 2-(5-bromo-2-fluorobenzyl)-1-benzothiophene may be added. The seed crystal added in this case can be produced as follows.

A dioxane (1.1 liters) solution of 2-[(5-bromo-2-fluorophenyl)(chloro)methyl]-1-benzothiophene (551 g) was added to a dioxane (3.3 liters)-water (1.6 liters) solution of sodium borohydride (410 g) and sodium hydroxide (31 g) at 60 to 66° C., followed by stirring at 52 to 60° C. for 39 hours. To the reaction mixture was added toluene (5.5 liter), water (3.8 liters) and 36% hydrochloric acid (620 ml) to conduct extraction. The organic layer was subjected to distillation under reduced pressure to distil off the solvent. The residue was dried under reduced pressure. The obtained crystals were dissolved in 2-propanol (1 liter) and methanol (1 liter) with heating, followed by stirring at 0° C. for 20.5 hours. The separated-out crystals were collected by filtration, washed with methanol (500 ml), and dried under reduced pressure to obtain 2-(5-bromo-2-fluorobenzyl)-1-benzothiophene [373 g, yield: 75.0%, purity: 99% (HPLC)] as white crystals. Incidentally, the 2-[(5-bromo-2-fluorophenyl)(chloro)methyl]-1-benzothiophene is the same as the compound (5) obtained in the second step of the production method of the present invention.

Next, the present invention method for producing a C-glycoside derivative represented by the formula (1), shown in the reaction formula (II) is described by way of Example. However, the present invention is not restricted to the Example; it can be easily modified or changed by those skilled in the art, as long as there is no deviation from the gist of the present invention; and, needless to say, modified or changed ones are included in the scope of the present invention.

Example

First step: Synthesis of
1-benzothien-2-yl(5-bromo-2-fluorophenyl)methanol

Into a tetrahydrofuran (100 liters) solution of benzo[b]thiophene (17.4 kg) was dropwise added a n-hexane solution (56.2 kg) of n-butyl lithium (15.08%) in an argon atmosphere at −24.2 to −13.5° C., followed by stirring at −22.1 to −13.5° C. for 40 minutes. Into this solution was dropwise added a tetrahydrofuran (18 liters) solution of 5-bromo-2-fluorobenzaldehyde (25.5 kg) at −22.1 to −11.8° C., followed by stirring at −23.5 to −16.1° C. for 2 hours. To the reaction mixture were added water (100 liters), toluene (130 liters) and 38% hydrochloric acid (12.3 kg), and extraction was conducted. The organic layer was washed with water (130 liters) and then subjected to distillation at normal pressure to distill off the solvent until the residue became 100 liters. Toluene (130 liters) was added to the residue and the mixture was subjected to distillation at normal pressure to distil off the solvent until the residue became 100 liters. The operation of adding toluene to the residue and subjecting the mixture to distillation under reduced pressure to distill off the solvent, was repeated twice: Then, n-heptane (310 liters) was added to the residue, followed by heating to dissolve the residue. To the solution was added, as a seed crystal, about 26 g of the 1-benzothien-2-yl(5-bromo-2-fluorophenyl)methanol produced in the same manner as that shown in the first step of Reference Example 1, followed by stirring at 1.2 to 5.0° C. for 13 hours. The separated-out crystals were collected by filtration, washed twice with a toluene-n-heptane (1:6) mixed solvent (26 liters), and subjected to vacuum drying to obtain, as white crystals, 1-benzothien-2-yl(5-bromo-2-fluorophenyl)methanol [35.91 kg, yield: 84.8%, purity: 99% (HPLC)].

¹H-NMR (CDCl₃): δ 2.74 (1H, d), 6.35 (1H, d), 6.93 (1H, dd), 7.14 (1H, s), 7.27-7.38 (2H, m), 7.39 (1H, m), 7.68 (1H, dd), 7.74 (2H, m)

Second step: Synthesis of 2-[(5-bromo-2-fluorophenyl)(chloro)methyl]-1-benzothiophene Into an acetonitrile (10 ml) solution of 1-benzothien-2-yl(5-bromo-2-fluorophenyl)methanol (1.0 g) was dropwise added thionyl chloride (706 mg) at a temperature of 5° C. or lower, followed by stirring at 5.0 to 25.0° C. for 3.5 hours. The reaction mixture was subjected to distillation under reduced pressure to distill off the solvent and the residue was subjected to vacuum drying to obtain 2-[(5-bromo-2-fluorophenyl)(chloro)methyl]-1-benzothiophene [1.05 g, yield: 100%, purity: 99% (HPLC)].

¹H-NMR (CDCl₃): δ 6.62 (1H, s), 6.98 (1H, dd), 7.22 (1H, s), 7.30-7.37 (2H, m), 7.45 (1H, m), 7.71 (1H, dd), 7.77 (1H, m), 7.81 (1H, dd)

Third step: Synthesis of
2-(5-bromo-2-fluorobenzyl)-1-benzothiophene

Acetonitrile (1,260 ml) was added to 2-[(5-bromo-2-fluorophenyl)(chloro)methyl]-1-benzothiophene (265.69 g) and the mixture was heated to 40° C. The resulting solution was added to a water (1,260 ml) solution of sodium borohydride (113.0 g) and sodium hydroxide (14.9 g) at 59.0 to 67.9° C., followed by stirring at 24.1 to 67.5° C. for 17.5 hours. To the reaction mixture were added 36% hydrochloric acid (340.5 g), water (1,260 ml) and toluene (1,260 ml), and extraction was conducted. The organic layer was washed with a 5% aqueous sodium hydrogencarbonate solution (1,260 ml) and subjected to vacuum distillation to distil off the solvent. To the residue were added 2-propanol (378 ml) and methanol (756 ml), and the residue was dissolved with heating. To the solution was added, as a seed crystal, 2.7 g of the 2-(5-bromo-2-fluorobenzyl)-1-benzothiophene produced by the method of Reference Example 2, at 39.7° C., followed by stirring at 0.7 to 5.0° C. for 13 hours. The separated-out crystals were collected by filtration, washed with methanol (251 ml), and vacuum-dried to obtain, as white crystals, 2-(5-bromo-2-fluorobenzyl)-1-benzothiophene [194.05 g, yield: 80.9%, purity: 99% (HPLC)].

$^1$H-NMR (CDCl$_3$): δ 4.18 (2H, s), 6.90-6.97 (1H, dd), 7.17 (1H, s), 7.22-7.40 (4H, m), 7.67 (1H, d), 7.74 (1H, d)

Fourth step: Synthesis of (1S)-2,3,4,6-tetra-O-acetyl-1,5-anhydro-1-[3-(1-benzothien-2-ylmethyl)-4-fluorophenyl]glucitol To a toluene (32.5 ml)-diisopropyl ether (25 ml) solution of 2-(5-bromo-2-fluorobenzyl)-1-benzothiophene (5.0 g) was dropwise added a n-hexane solution (10 ml) of n-butyl lithium (1.6 M) at −43.5 to −33.3° C., followed by stirring for 10 minutes. To the reaction mixture was added, at −72.6 to −65.0° C., a toluene (17.5 ml) solution of 2,3,4,6-tetrakis-O-(trimethylsilyl)-D-glucono-1,5-lactone (8.0 g), followed by stirring for 6 hours. The reaction mixture was added to a methanol (25 ml) solution of an ethyl acetate solution (7.8 ml) of hydrogen chloride (4 M) at a temperature of 0° C. or lower, followed by stirring at 0° C. for 17 hours. The reaction mixture was added to a water (35 ml) solution of potassium carbonate (1.29 g). Thereto was added ethyl acetate, followed by extraction. The aqueous layer was extracted with toluene (20 ml)-ethyl acetate (10 ml). The organic layers obtained by extraction were combined and subjected to vacuum distillation to distil off the solvent until the reside became 40 ml. Toluene (25 ml) was added to the residue and the mixture was subjected to vacuum distillation to distil off the solvent until the residue became 40 ml. This operation of adding toluene to the residue and subjecting the mixture to vacuum distillation to distil off the solvent, was repeated twice to obtain methyl 1-C-[3-(1-benzothien-2-ylmethyl)-4-fluorophenyl]-α-glucopyranoside as a toluene solution.

$^1$H-NMR (CD$_3$OD): δ 3.08 (3H, s), 3.10 (1H, m), 3.42 (1H, dd), 3.58 (1H, m), 3.75 (1H, dd), 3.82 (1H, m), 3.92 (1H, dd), 4.23 (1H, d), 4.32 (1H, d), 7.05 (1H, s), 7.09 (1H, dd), 7.22 (1H, m), 7.27 (1H, m), 7.54 (1H, m), 7.64-7.65 (2H, m), 7.72 (1H, d)

To the above-obtained toluene solution of methyl 1-C-[3-(1-benzothien-2-ylmethyl)-4-fluorophenyl]-α-glucopyranoside were added pyridine (7.39 g) and 4-dimethylaminopyridine (19 mg). Thereto was added acetic anhydride (7.94 g) at 1.7 to 3.3° C., followed by stirring at room temperature for 12 hours. To the reaction mixture was added hydrochloric acid (2 M, 50 ml), followed by extraction. The organic layer was washed with a 5% aqueous sodium hydrogencarbonate solution (75 ml) and successively with an aqueous sodium chloride solution (25%, 50 ml), and subjected to vacuum distillation to distil off the solvent until the residue became 15 ml, to obtain, as a toluene solution, methyl 2,3,4,6-tetra-O-acetyl-1-C-[3-(1-benzothien-2-ylmethyl)-4-fluorophenyl]-α-glucopyranoside.

$^1$H-NMR (CD$_3$OD): δ 1.67 (3H, s), 1.90 (3H, s), 2.02 (3H, s), 2.03 (3H, s), 3.13 (3H, s), 4.07 (1H, m), 4.25-4.32 (2H, m), 4.37-4.40 (2H, m), 4.86 (1H, m), 5.15 (1H, dd), 5.51 (1H, dd), 7.00 (1H, s), 7.15 (1H, dd), 7.24 (1H, dd), 7.29 (1H, dd), 7.42 (2H, m), 7.66 (1H, d), 7.72 (1H, d)

Acetonitrile (10 ml) was added to the residue obtained above. The solution was added to an acetonitrile (20 ml) solution of trifluoromethanesulfonic acid (4.67 g) and tert-butyldimethylsilane (3.62 g) at −9.2 to 1.0° C., followed by stirring at 0° C. for 3 hours. To the reaction mixture were added tetrahydrofuran (70 ml) and toluene (25 ml). The solution was added to a solution of potassium carbonate (2.8 g), sodium chloride (1.5 g) and water (30 ml) at 5.0 to 9.0° C., followed by extraction at 30 to 40° C. The organic layer was washed with a 25% aqueous sodium chloride solution (25 ml) and subjected to distillation at normal pressure to distil off the solvent until the residue became 55 ml. The residue was cooled slowly and stirred at 0° C. for 50 hours. The separated-out crystals were collected by filtration, washed twice with toluene (5 ml) and vacuum-dried to obtain, as white crystals, 1S)-2,3,4,6-tetra-O-acetyl-1,5-anhydro-1-[3-(1-benzothien-2-ylmethyl)-4-fluorophenyl]glucitol [6.66 g, yield: 74.7%, purity: 99% (HPLC)].

$^1$H-NMR (CDCl$_3$): δ 1.70 (3H, s), 1.98 (3H, s), 2.04 (3H, s), 2.05 (3H, s), 3.78 (1H, m), 4.12-4.38 (5H, m), 5.07 (1H, m), 5.18-5.31 (2H, m), 6.99 (1H, dd), 7.07 (1H, dd), 7.20-7.32 (4H, m), 7.66 (1H, d), 7.73 (1H, d)

Fifth step: Synthesis of (1S)-1,5-anhydro-1-C-[3-(1-benzothiophene-2-ylmethyl)-4-fluorophenyl]-D-glucitol To a methanol (427.4 kg) solution of (1S)-2,3,4,6-tetra-O-acetyl-1,5-anhydro-1-[3-(1-benzothien-2-ylmethyl)-4-fluorophenyl]glucitol (76.9 kg) was added a water (230 liters) solution of sodium hydroxide (26.9 kg) at a temperature of 25° C. or lower, followed by stirring at 40.0 to 49.1° C. for 4 hours. Water (850 liters) was added to the reaction mixture, and 12.9 kg of 38% hydrochloric acid was added thereto at a temperature of 25° C. or lower. The mixture was heated to 60° C., followed by stirring at 20.2 to 25.0° C. for 9.5 hours. The separated-out crystals were collected by filtration, washed with tap water (80 liters), and vacuum-dried to obtain, as white crystals, (1S)-1,5-anhydro-1-C-[3-(1-benzothiophene-2-ylmethyl)-4-fluorophenyl]-D-glucitol [52.7 kg, yield: 97.0%, purity: 99% (HPLC)].

$^1$H-NMR (CD$_3$OD): δ 3.29-3.48 (4H, m), 3.68 (1H, dd), 3.87 (1H, dd), 4.11 (1H, d), 4.20-4.29 (2H, m), 7.03 (1H, s), 7.08 (1H, dd), 7.19-7.29 (2H, m), 7.35 (1H, m), 7.42 (1H, dd), 7.64 (1H, d), 7.72 (1H, d)

The yield of the production method of the present invention, in Example is shown in the following Table 1.

TABLE 1

|  | Yield |
|---|---|
| First step | 84.8% |
| Second step | 100% |
| Third step | 80.9% |
| Fourth step | 74.7% |
| Fifth step | 97.0% |
| Overall yield | 49.7% |

Meanwhile, the yield of the known production method of C-glycoside derivative represented by the formula (1), in Reference Example 1 is shown in the following Table 2.

TABLE 2

|  | Yield |
| --- | --- |
| First step | 83.6% |
| Second step | 78.0% |
| Third step | 50.2% |
| Fourth step | 74.7% |
| Fifth step | 30.2% |
| Sixth step | 87.8% |
| Overall yield | 6.48% |

As is understood from Table 1 and Table 2, the present invention method, as compared with the known method, includes no step giving a yield of 50% or lower; therefore, the present invention method can give a high total yield and is advantageous in cost. Further, the present invention method has no need of using a column or chloroform. For these reasons, the present invention method, as compared with the known method, is extremely superior industrially. In particular, the present invention method has achieved a high overall yield of 49.7%, whereby an industrially applicable production method has been established. Incidentally, the first step in Example and the first step in Reference Example 1 conduct the same reaction; however, they give slightly different yields. Even if the yield of the first step of Example is used as the yield of the first step of Reference Example 1 and the overall yield of the Reference Example 1 is calculated, the overall yield thereof becomes 6.58%; thus, the overall yield of Example is overwhelmingly superior and there has been established, by the present invention method, an industrially applicable production method of C-glycoside derivative represented by the formula (1).

INDUSTRIAL APPLICABILITY

The present invention provides a method for producing a C-glycoside derivative, which enables the production at a high yield at a low cost, which conforms to environmental protection, and which is advantageous industrially; and an intermediate for synthesis, useful in the production step of the method.

The invention claimed is:

1. A method for producing a compound represented by the following formula (1),

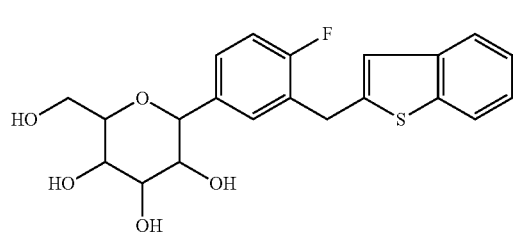

comprising subjecting a compound represented by the following formula (2d)

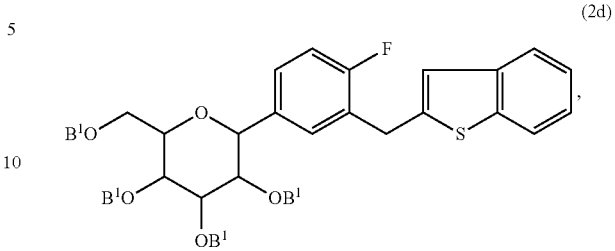

wherein each $B^1$ may be the same or different from each other and each is H or $C(=O)R^1$, and each $R^1$ may be the same or different from each other and each is a lower alkyl, with the proviso that at least one $B^1$ is $C(=O)R^1$, to a reaction for elimination of an acyl group in the presence of a base and a solvent, and purifying the compound of formula (1) by a method other than column chromatography.

2. A method according to claim 1, wherein the compound of formula (2d) is produced by allowing a compound selected from the group consisting of triethylsilane, triisopropylsilane, tert-butyldimethylsilane, sodium borohydride and sodium tri(acetoxy)borohydride to act on a compound represented by the following formula (2c)

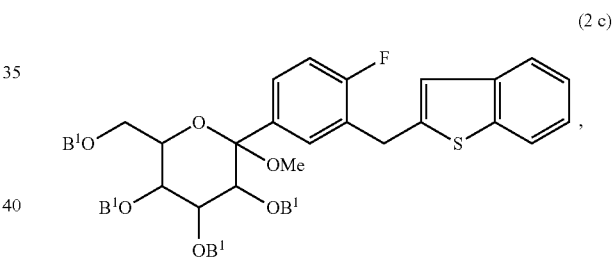

wherein each $B^1$ may be the same or different from each other and each is H or $C(=O)R^1$, each $R^1$ may be the same or different from each other and each is a lower alkyl, and Me is methyl, with the proviso that at least one $B^1$ is $C(=O)R^1$, to reduce the compound of the formula (2c).

3. A method for producing a compound represented by the following formula (1),

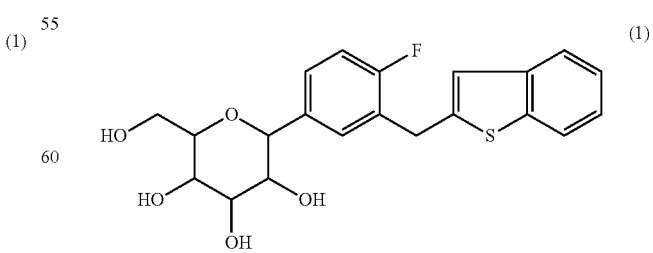

comprising subjecting a compound represented by the following formula (2d)

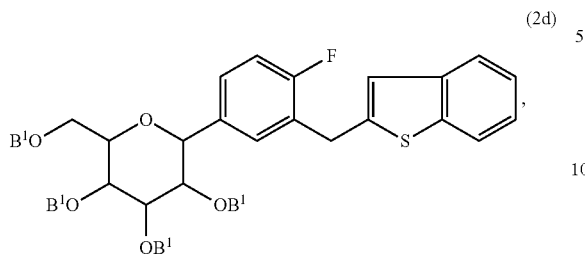

wherein each $B^1$ may be the same or different from each other and each is H or $C(=O)R^1$, and each $R^1$ is methyl, with the proviso that at least one $B^1$ is $C(=O)R^1$, to a reaction for elimination of an acetyl group, in the presence of a base and a solvent, and purifying the compound of formula (1) by a method other than column chromatography.

4. A method for producing a compound represented by the following formula (1),

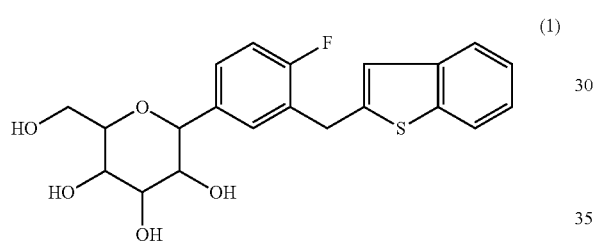

comprising subjecting a compound represented by the following formula (4)

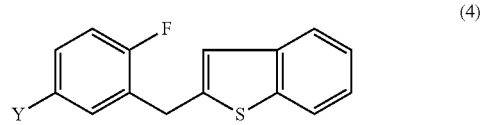

wherein Y is Br or I, and a compound represented by the following formula (3)

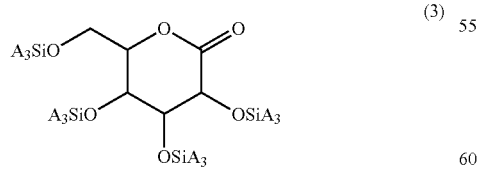

wherein each A may be the same or different from each other and each is a lower alkyl, to an addition reaction, eliminating tri-lower alkyl silyl, and being acylated, then conducting reduction to obtain a compound represented by the following (formula 2d)

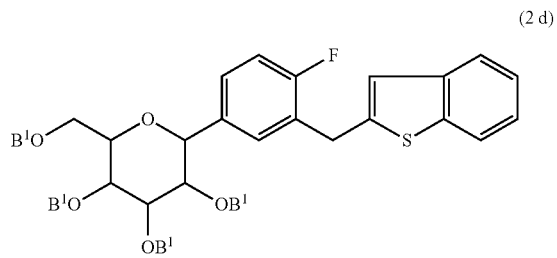

wherein each $B^1$ may be the same or different from each other and each is H or $C(=O)R^1$, and each $R^1$ may be the same or different from each other and each is a lower alkyl, with the proviso that at least one $B^1$ is $C(=O)R^1$, and subjecting the compound to a reaction for elimination of an acyl group.

5. A method according to claim 4, wherein the compound represented by the formula (4) is obtained by subjecting a compound represented by the following formula (5)

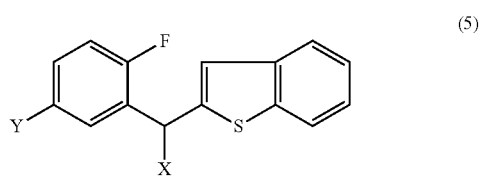

wherein X is halogen and Y is Br or I, to a reduction reaction.

6. A method for producing a compound represented by the following formula (1),

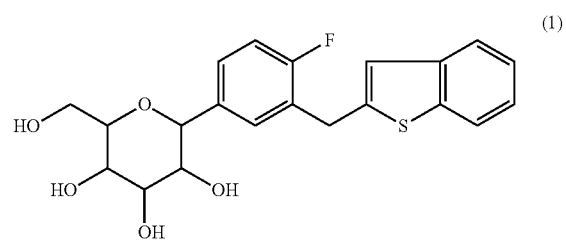

comprising subjecting a compound represented by the following formula (4)

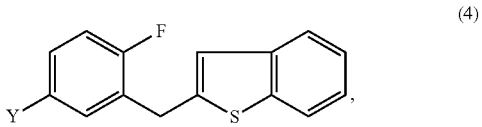

wherein Y is Br or I, and a compound represented by the following formula (3a)

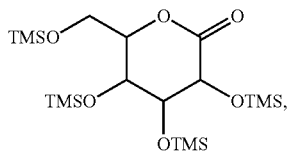
(3a)

wherein TMS is trimethylsilyl, to an addition reaction, eliminating trimethylsilyl in methanol, and being acetylated, then conducting reduction to obtain a compound represented by the following formula (2a)

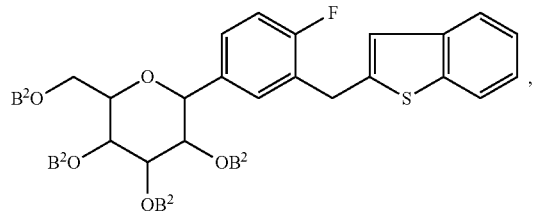
(2a)

wherein each $B^2$ may be the same or different from each other and each is H or C(=O)Me, and Me is methyl, with the proviso that at least one $B^2$ is C(=O)Me, and subjecting the compound to a reaction for elimination of acetyl group.

7. A method according to claim 6, wherein the compound represented by the formula (4) is obtained by subjecting a compound represented by the following formula (5)

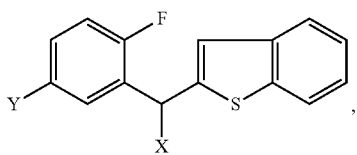
(5)

wherein X is halogen and Y is Br or I, to a reduction reaction.

* * * * *